United States Patent
Han et al.

(10) Patent No.: US 12,120,996 B2
(45) Date of Patent: Oct. 22, 2024

(54) **INDUCTION METHOD FOR IMPROVING YIELD AND FERTILITY OF 2N POLLEN IN *CAMELLIA OLEIFERA***

(71) Applicant: Central South University of Forestry and Technology, Changsha (CN)

(72) Inventors: Zhiqiang Han, Changsha (CN); Hongda Deng, Changsha (CN); Xiaoyu Zhang, Changsha (CN); Hailang Tong, Changsha (CN); Xing Liu, Changsha (CN); Tongyue Zhang, Changsha (CN)

(73) Assignee: CENTRAL SOUTH UNIVERSITY OF FORESTRY & TECHNOLOGY, Changsha (CN)

( * ) Notice: Subject to any disclaimer, the term of this patent is extended or adjusted under 35 U.S.C. 154(b) by 0 days.

(21) Appl. No.: 18/407,908

(22) Filed: Jan. 9, 2024

(65) Prior Publication Data

US 2024/0237599 A1    Jul. 18, 2024

(51) Int. Cl.
  *A01H 1/08*    (2006.01)

(52) U.S. Cl.
  CPC .................................... *A01H 1/08* (2013.01)

(58) Field of Classification Search
  None
  See application file for complete search history.

(56) References Cited

PUBLICATIONS

Zhang et al 2021 (Physiol Mol Biol Plants 27:5 p. 959-968) (Year: 2021).*
Yao et al 2017 (Forests 8:152 p. 1-14) (Year: 2017).*
Qi et al 2018 (Molecules 23: 386 p. 1-14) (Year: 2018).*
Ghuge et al 2015 (Plant Physiology 168: p. 690-707) (Year: 2015).*
Paupière et al 2014 (Metabolites 4: p. 889-920) (Year: 2014).*
Zhang et al., Cytological and morphology characteristics of natural microsporogenesis within Camellia oleifera, Physiol Mol Biol Plants, 2021, pp. 1-10.
Wang et al., High temperature-induced production of unreduced pollen and its cytological effects in Populus, Scientific Reports | 7: 528, pp. 1-12.
Mai et al., High temperature treatment generates unreduced pollen in persimmon (Diospyros kaki Thunb.), Scientia Horticulture, 258, 201, pp. 1-7.
Zhao et al., Relationship of ROS accumulation and superoxide dismutase isozymes in developing anther with floret fertility of rice under heat stress, Plant Physiology and Biochemistry, 122, 2018, pp. 90-101.
Curtis et al., N,N'-Dimethylthiourea dioxide formation from NN'-dimethylthiourea reflects hydrogen peroxide concentrations in simple biological systems, Proc. Natl. Acad. Sci. USA, vol. 85, pp. 3422-3425, May 1988 Cell Biology.
Office action for 202310035477.2, issued on Oct. 19, 2023, translated pp. 1-5.
Chinese Office action for 202310035477.2, issued on Oct. 19, 2023, pp. 1-3.

* cited by examiner

*Primary Examiner* — Matthew R Keogh
(74) *Attorney, Agent, or Firm* — Nicholas Pfeifer; Smith & Hopen, P. A.

(57) ABSTRACT

The present disclosure relates to an induction method for improving a yield and fertility of 2n pollen in *Camellia oleifera*, including: subjecting a flower branch of the *Camellia oleifera* to a high-temperature treatment when a style length L of the *Camellia oleifera* develops to 1.97 mm<L≤2.57 mm. The method specifically includes: applying N,N'-dimethylthiourea (DMTU) or a DMTU-based mixed solution to the *Camellia oleifera* at a meiosis stage, and then conducting the high-temperature treatment to induce production of 2n pollen. In the method of the present disclosure, the application of the high-temperature treatment precursor to the *Camellia oleifera* before the high-temperature treatment can significantly improve a fertility rate of 2n pollen.

5 Claims, 3 Drawing Sheets

INDUCTION METHOD FOR IMPROVING YIELD AND FERTILITY OF 2N POLLEN IN CAMELLIA OLEIFERA

CROSS REFERENCE TO RELATED APPLICATION

This patent application claims the benefit and priority of Chinese Patent Application No. 202310035477.2, filed with the China National Intellectual Property Administration on Jan. 10, 2023, the disclosure of which is incorporated by reference herein in its entirety as part of the present application.

TECHNICAL FIELD

The present application belongs to the technical field of ploidy breeding of *Camellia oleifera*, and specifically relates to a method for inducing 2n pollen in *Camellia oleifera* based on a high-temperature treatment precursor, and a use thereof.

BACKGROUND

*Camellia oleifera* is an important oil-bearing woody plant species in southern China, which plays an important role in ensuring the grain and oil safety of China and has a great breeding potential. The inventors have found in previous work on ploidy breeding of *Camellia oleifera* that *Camellia oleifera* can produce natural 2n pollen, but an occurrence frequency of natural 2n pollen is as low as 0.9% (Zhang XY. et al. Cytological and morphology characteristics of natural microsporogenesis within *Camellia oleifera*. Physiology and Molecular Biology of Plants, 2021, 27 (5): 959-968), which is difficult to meet the need of polyploidy breeding of *Camellia oleifera*.

In the plant kingdom, a mutagenic agent can be used to artificially induce the production of 2n pollen, and a high-temperature treatment is widely used as a physical induction method for ploidy breeding of forest trees such as poplars, *Eucommia ulmoides*, and *Diospyros kaki* (Tian Mengdi et al. High-Temperature Induction of Pollen Chromosome Doubling of *Populus canescens* to Create Hybrid Triploid. Scientia Silvae Sinicae, 2018, 54 (03): 39-47; Wang J. et al. High temperature induced production of unreduced pollen and its cytological effects in *Populus*. Scientific Reports, 2017, 7 (1): 1-12; Li Yun et al. High-Temperature Induction of Embryo Sac Chromosome Doubling to Breed *Eucommia ulmoides* Triploid.

Molecular Plant Breeding, 2018, 16 (17): 5743-5751; and Mai Y. et al. High temperature treatment generates unreduced pollen in persimmon (*Diospyros kaki* Thunb.). Scientia Horticulturae, 2019, 258:108774.) to obtain a batch of novel polyploid forest tree germplasms. However, a high temperature, as a stress, may destroy the auxin synthesis and metabolic activities of reproductive organs, increase the accumulation of reactive oxygen species in reproductive organs, destroy the glucose metabolism, lead to the failure of microspore development, reduce the pollen fertility, and inhibit the anther dehiscence, thereby causing a low pollen yield and even abortion (Hu Qiuqian et al. High-Temperature Injury Mechanism for Fertility of *Oryza sativa* Spikelet and Corresponding Cultivation Control Measure [J]. Plant Physiology Journal, 2020, 56 (06): 1177-1190; Zhang Zaibao et al. Effect of High-Temperature Stress on Anther Development and Signal Transduction Network. Journal of Biology, 2019, 36 (01): 92-95; and Zhao Q. et al. Relationship of ROS accumulation and superoxide dismutase isozymes in developing anther with floret fertility of rice under heat stress. Plant Physiology and Biochemistry. 2018, 122:90-101).

During exploration of a method for high-temperature induction of 2n pollen in *Camellia oleifera*, the inventors have also found that an abortion rate of 2n pollen after a high-temperature treatment can be up to 90.0%, and the high abortion rate of 2n pollen will cause a significant decline in an efficiency of 2n pollen hybridization to produce polyploids, which severely limits the application of high-temperature induction of 2n pollen in polyploidy breeding of *Camellia oleifera*. Therefore, there is an urgent need to establish a high-temperature treatment method that can ensure the fertility of 2n pollen in *Camellia oleifera*.

N,N'-Dimethylthiourea (DMTU) is a strong penetrating molecule isolated from black garlic, and is an orally-effective hydroxyl radical (·OH) scavenger. DMTU blocks the generation of ·OH in vitro by activating neutrophils. DMTU can play the antioxidant roles including ·OH— scavenging and anti-inflammatory roles to prevent a rat gastric mucosa injury induced by water immersion restraint stress (WIRS), and can also clear the accumulation of reactive oxygen species in lungs of a rat to reduce a body injury (Curtis W. et al. N,N'-dimethylthiourea dioxide formation from N,N'-dimethylthiourea reflects hydrogen peroxide concentrations in simplebiological systems. Proceedings of the National Academy of Sciences, 1988, 85 (10): 3422-3425).

SUMMARY

In view of the technical problems in the existing methods for induction of 2n pollen, the present disclosure determines effective treatment stages and treatment conditions for high-temperature induction of pollen chromosome doubling of *Camellia oleifera*, and provides a method for improving a yield and fertility of 2n pollen in *Camellia oleifera*. In the method of the present disclosure, based on a high-temperature treatment, a high-temperature treatment precursor is applied to a flower branch of *Camellia oleifera* to be treated, that is, the high-temperature treatment precursor is applied before the high-temperature treatment to allow a high 2n pollen yield with a high fertile 2n pollen proportion.

The technical solution to be solved by the present disclosure is implemented by the following technical solutions:

The present disclosure provides an induction method for improving a yield and fertility of 2n pollen in *Camellia oleifera*, including: subjecting a flower branch of the *Camellia oleifera* to a high-temperature treatment when a style length L of the *Camellia oleifera* develops to 1.97 mm<L≤2.57 mm.

The high-temperature treatment is conducted at 43° C. to 49° C., preferably 45° C. to 47° C., and more preferably 45° C.; and the high-temperature treatment is conducted for 3 h to 6 h, preferably 4 h to 5 h, and more preferably 4 h.

In particular, a variety of the *Camellia oleifera* is one or more selected from the group consisting of *Camellia oleifera* 'Huashuo', *Camellia oleifera* 'Huajin', and *Camellia oleifera* 'Huaxin', and is preferably *Camellia oleifera* 'Huaxin'.

The high-temperature treatment is conducted when the style length L of the *Camellia oleifera* develops to 1.97 mm<L≤2.27 mm, and preferably, the high-temperature treatment is conducted when the style length L of the *Camellia oleifera* develops to 1.97 mm<L≤2.17 mm.

In particular, the method further includes: before the high-temperature treatment, spraying a high-temperature treatment precursor on the flower branch of the *Camellia oleifera* or injecting the high-temperature treatment precursor into a flower bud on the flower branch of the *Camellia oleifera*.

The high-temperature treatment precursor is a DMTU-containing solution.

In particular, the DMTU-containing solution is a DMTU solution or a DMTU-containing mixed solution including the following components: DMTU: 5 mg/L to 20 mg/L, mannitol: 0.1 g/L to 2.0 g/L, ascorbic acid: 0.5 mg/L to 2.0 mg/L, brassinolide: 2.0 mg/L to 8.0 mg/L, and sucrose: 5.0 g/L to 30.0 g/L.

In particular, a concentration of DMTU in the DMTU solution is 5 mg/L to 20 mg/L and preferably 10 mg/L.

In particular, the DMTU-containing mixed solution includes the following components: the DMTU: 10 mg/L, the mannitol: 0.5 g/L, the ascorbic acid: 1.0 mg/L, the brassinolide: 4.0 mg/L, and the sucrose: 15.0 g/L.

In particular, the method further includes: before the high-temperature treatment is conducted and after the high-temperature treatment precursor is sprayed or injected, wrapping the flower branch of the *Camellia oleifera*.

In particular, before the high-temperature treatment is conducted and after the high-temperature treatment precursor is sprayed or injected, the flower branch of the *Camellia oleifera* is wrapped with a plastic film.

In addition, the present disclosure provides a method for improving a yield and fertility of 2n pollen in *Camellia oleifera*, including the following steps: determining a correspondence between a meiosis stage of pollen mother cells and a flower bud/style length of the *Camellia oleifera* through cytological observation, and conducting a high-temperature treatment when a flower bud/style develops to a specified length to induce production of 2n pollen of the *Camellia oleifera* and improve an occurrence frequency and fertility of 2n pollen.

In order to allow an excellent induction effect, the high-temperature treatment applied to a flower branch of the *Camellia oleifera* is conducted at 43° C. to 49° C., preferably 45° C. to 47° C., and more preferably 45° C.; and the high-temperature treatment applied to a flower branch of the *Camellia oleifera* is conducted for 3 h to 6 h, preferably 4 h to 5 h, and more preferably 4 h.

Preferably, when a style of the *Camellia oleifera* develops to a length L of 1.97 mm<L≤2.57 mm, the high-temperature treatment is applied to a flower branch of the *Camellia oleifera*, which can increase a yield of 2n pollen; more preferably, when a style of the *Camellia oleifera* develops to a length L of 1.97 mm<L≤2.27 mm (a leptotene stage to a diakinesis stage), the high-temperature treatment is applied; and most preferably, when a style of the *Camellia oleifera* develops to a length L of 1.97 mm<L≤2.17 mm (a leptotene stage to a pachytene stage), the high-temperature treatment is applied, which allows the optimal 2n pollen induction effect.

In the method of the present disclosure, a meiosis process of pollen mother cells of *Camellia oleifera* is determined in real time based on a style length (L). That is, when the style length of *Camellia oleifera* develops to 1.97 mm<L≤2.57 mm, pollen mother cells are mainly in a meiosis stage; when the style length of *Camellia oleifera* develops to 1.97 mm<L≤2.17 mm, pollen mother cells are mainly in a leptotene stage to a pachytene stage; when the style length of *Camellia oleifera* develops to 2.17 mm<L≤2.27 mm, pollen mother cells are mainly in a diplotene stage to a diakinesis stage; when the style length of *Camellia oleifera* develops to 2.27 mm<L≤2.37 mm, pollen mother cells are mainly in a metaphase I to a telophase I; when the style length of *Camellia oleifera* develops to 2.37 mm<L≤2.57 mm, pollen mother cells are mainly in a prophase II to an anaphase II; and when the style length of *Camellia oleifera* develops to 2.57 mm<L≤2.87 mm, pollen mother cells are mainly in a tetrad stage.

A variety of the *Camellia oleifera* is preferably *Camellia oleifera* 'Huaxin'.

The "mainly" means that a percentage of pollen mother cells at a corresponding development stage in total pollen mother cells is significantly higher than a percentage of pollen mother cells at other stages in total pollen mother cells.

The method of the present disclosure can increase an accuracy of treatment stage selection and the stability of an induction effect during pollen chromosome doubling induced by a high-temperature treatment, and improve an induction efficiency for 2n pollen in *Camellia oleifera*.

The high-temperature treatment precursor is a solution including DMTU, mannitol, ascorbic acid, and brassinolide, and is preferably a DMTU solution with a concentration of 10 mg/L.

The DMTU solution is applied through injection into a flower bud or spraying on a flower branch. Preferably, the DMTU solution is injected into a flower bud until water droplets ooze out from the flower bud.

Immediately after the high-temperature treatment precursor is sprayed on a flower branch, the sprayed flower branch is wrapped with a plastic film; or immediately after the high-temperature treatment precursor is injected into a flower bud, the whole flower branch on which the flower bud is located is wrapped with a plastic film. This operation can prevent an injected solution from evaporating rapidly due to a high-temperature treatment and thus losing its effect.

Further, in order to improve a fertility rate of 2n pollen obtained after a high-temperature treatment to a great extent, the present disclosure adopts an orthogonal design method to optimize a composition of the high-temperature treatment precursor and thus propose an optimal composition of the high-temperature treatment precursor. The optimal composition of the high-temperature treatment precursor includes the following components:

DMTU at a concentration of 5 mg/L to 20 mg/L and preferably 10 mg/L;

mannitol at a concentration of 0.1 g/L to 2.0 g/L and preferably 0.5 g/L;

ascorbic acid at a concentration of 0.5 mg/L to 2.0 mg/L and preferably 1.0 mg/L;

brassinolide at a concentration of 2.0 mg/L to 8.0 mg/L and preferably 4.0 mg/L; and sucrose at a concentration of 5.0 g/L to 30.0 g/L and preferably 15 g/L.

The present disclosure has the following beneficial effects:

(1) The method of the present disclosure for the first time clarifies an optimal stage for high-temperature induction of production of 2n pollen in *Camellia oleifera*, and determines an appropriate temperature and a continuous treatment time of high-temperature induction. The method of the present disclosure can improve an induction efficiency of 2n pollen in *Camellia oleifera*, and can improve a yield of 2n pollen from 0.9% under natural conditions to 12.59%, which can promote the progress of ploidy breeding of *Camellia oleifera*.

(2) The method of the present disclosure for the first time proposes the determination of a meiosis process of pollen mother cells of *Camellia oleifera* based on a style length in real time, which allows the rapid and accurate control of a meiosis stage and avoids the problem that the optimal treatment stage is missed due to time consumption of cytological experimental observation of a meiosis process. Therefore, the method of the present disclosure has strong operability, and can effectively save the experimental materials, reagents, manpower, and time required for observation of a meiosis process.

(3) The present disclosure discovers for the first time that DMTU has a significant improvement effect on fertility of 2n pollen induced by a high-temperature treatment, and proposes a formula and use of a DMTU-based high-temperature treatment precursor of *Camellia oleifera*. The high-temperature treatment precursor can greatly improve a fertility rate of 2n pollen in *Camellia oleifera*, and allow a fertility rate of 96.82% for 2n pollen induced by a high-temperature treatment, which solves the problem that a high-temperature treatment reduces the pollen fertility and meets the need of ploidy breeding of *Camellia oleifera*.

BRIEF DESCRIPTION OF THE DRAWINGS

The accompanying drawings are provided for further comprehension of the present disclosure and constitute a part of the specification. The accompanying drawings, together with the embodiments of the present disclosure, are intended to explain rather than limit the present disclosure.

DETAILED DESCRIPTION OF THE EMBODIMENTS

Figure 1:
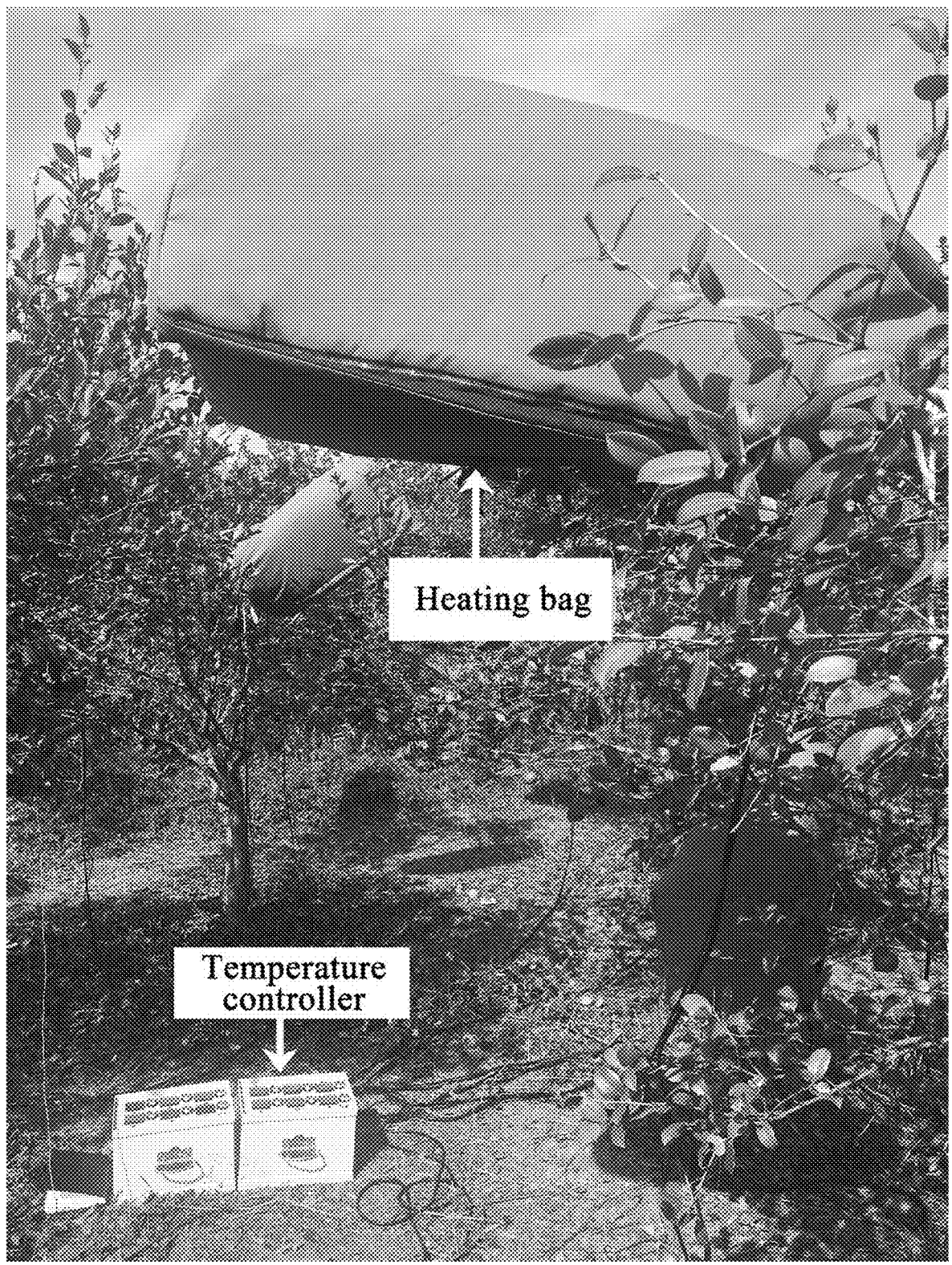
FIG. 1 shows the induction of 2n pollen in *Camellia oleifera* by a high-temperature treatment, where the arrows represent a heating bag and a temperature controller, respectively.

In order to specifically elaborate the design idea with universality of the present disclosure, specific experimental parameters are shown as examples below, but should not limit the protection scope of the present disclosure. All experimental methods used in the following examples are conventional methods, unless otherwise specified. All materials and reagents used in the following examples may be commercially available, unless otherwise specified.

Experimental *Camellia oleifera* materials used in the examples are non-ex vivo flower branches with healthy flower buds of *Camellia oleifera* 'Huaxin' selected by a research group from the Wangcheng base in Changsha City, Hunan Province.

Example 1 Screening of Technical Conditions of Pollen Chromosome Doubling of *Camellia oleifera*

1.1 Real-Time Determination of a Meiosis Stage of Pollen Mother Cells

The inventors have found during observation of a meiosis process of pollen mother cells that, when styles grow to a same length range, pollen mother cells are not all in a same meiosis stage, indicating that there is asynchrony of meiosis of pollen mother cells of *Camellia oleifera*. Different meiosis stages can be observed in a specified style length range, but meiosis stages of most pollen mother cells are relatively consistent. As a style continues to grow, a proportion of pollen mother cells in a meiosis anaphase gradually increases, indicating that there is a specified correlation between a meiosis stage and a style length.

Flower buds were collected, and lengths of styles in the flower buds were measured. Anthers were stained by an aceto-carmine staining method, temporary smears were made, and a meiosis process of pollen mother cells of *Camellia oleifera* was observed under an ordinary optical microscope.

Observation results are shown in Table 1: A style length (L) ranges from 1.97 mm to 2.87 mm at a leptotene stage to a tetrad stage, where when a style length is greater than 1.97 mm and less than or equal to 2.17 mm, pollen mother cells are mainly in a leptotene stage to a pachytene stage;

when a style length is greater than 2.17 mm and less than or equal to 2.27 mm, pollen mother cells are mainly in a diplotene stage to a diakinesis stage;

when a style length is greater than 2.27 mm and less than or equal to 2.37 mm, pollen mother cells are mainly in a metaphase I to a telophase I;

when a style length is greater than 2.37 mm and less than or equal to 2.57 mm, pollen mother cells are mainly in a prophase II to an anaphase II; and when a style length is greater than 2.57 mm and less than or equal to 2.87 mm, pollen mother cells are mainly in a tetrad stage.

Table 1 Relationship between a flower bud/style length and a meiosis process of pollen mother cells in *Camellia oleifera*

TABLE 1

Relationship between a flower bud/style length and a meiosis process of pollen mother cells in *Camellia oleifera*

| Style length L (mm)a | Proportions of pollen mother cells at different meiosis stages | | | | | | Number of flower buds observed |
|---|---|---|---|---|---|---|---|
| | Spore mother cells | Leptotene stage-Pachytene stage | Diplotene stage-Diakinesis stage | Metaphase I-Anaphase II | Prophase II-anaphase II | Tetrad stage | |
| L ≤ 1.97 | 0.69 | 0.13 | 0.02 | 0.06 | 0.10 | / | 310 |
| 1.97 < L ≤ 2.17 | 0.31 | 0.43 | 0.17 | 0.04 | 0.05 | / | 243 |
| 2.17 < L ≤ 2.27 | 0.20 | 0.28 | 0.41 | 0.06 | 0.05 | / | 231 |
| 2.27 < L ≤ 2.37 | 0.11 | 0.23 | 0.20 | 0.42 | 0.19 | / | 258 |
| 2.37 < L ≤ 2.57 | 0.06 | 0.13 | 0.14 | 0.18 | 0.39 | 0.10 | 235 |
| 2.57 < L ≤ 2.87 | / | / | 0.07 | 0.14 | 0.18 | 0.41 | 341 |

L represents a style length and a represents an average value.

1.2 Doubling Treatment

When style lengths of *Camellia oleifera* developed to be greater 1.97 mm, flower branches with a style length of 1.97 mm<L≤2.17 mm (a leptotene stage to a pachytene stage), 2.17 mm<L≤2.27 mm (a diplotene stage to a diakinesis stage), 2.27 mm<L≤2.37 mm (a metaphase I to an anaphase II), and 2.37 mm<L≤2.57 mm (a prophase II to an anaphase II) were selected as flower branches to be treated to obtain four treatment groups, which were denoted as a first treatment group, a second treatment group, a third treatment group, and a fourth treatment group, respectively.

As shown in FIG. 1, a heating bag of a non-ex vivo tree branch bud heating device (patent ZL200610113448.X) was sleeved on a flower branch to be treated in each treatment group through an open end, and the open end of a bag body was tightly sealed by a flexible rope wrapping around the flower branch.

In a specific embodiment of the present disclosure, a target flower branch was subjected to a high-temperature treatment with the non-ex vivo tree branch bud heating device (patent ZL200610113448.X) as an example. Other methods, devices, and apparatuses for a high-temperature treatment of a flower branch in the art are applicable to the present disclosure.

A bag body of each heating bag was connected to a temperature controller through a wire, and energized for heating to allow a high-temperature treatment. That is, the heating bag was heated by the temperature controller to a preset temperature (43° C., 45° C., 47° C., and 49° C.) and kept at this temperature for 3 h, 4 h, 5 h, and 6 h, and then the heating bag was removed to release the high-temperature treatment. An orthogonal experimental design was adopted for a treatment, and each treatment combination was numbered and recorded.

Untreated flower branches were adopted as a control group (CK group).

1.3 Statistical Analysis of a 2n Pollen Yield and Fertility

After the high-temperature treatment was released, *Camellia oleifera* grew naturally until anthers were pollinated. Pollen of each treatment was collected, and a temporary smear of the pollen was made by an aceto-carmine staining method and then photographed by an OlympusDP70 optical microscope; and a diameter of pollen in a temporary smear of each treatment was measured by Image J software, and a yield and a fertility rate of 2n pollen were counted.

Figure 2:
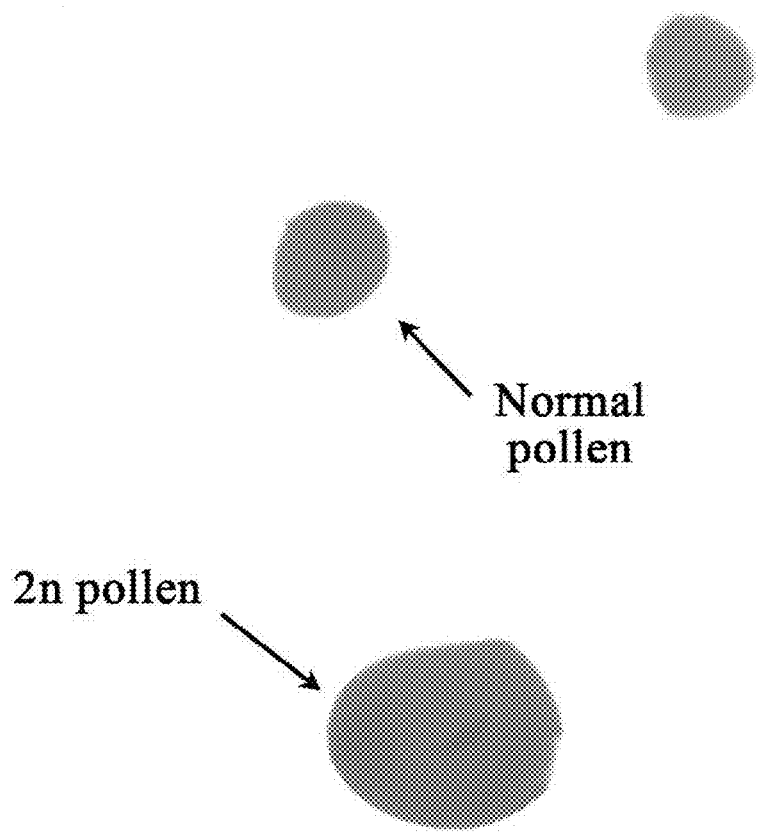
FIG. 2 shows morphologies of 2n pollen obtained after a high-temperature treatment and normal pollen, where large pollen represents the 2n pollen obtained after a high-temperature treatment and small pollen represents the normal pollen.
Figure 3:
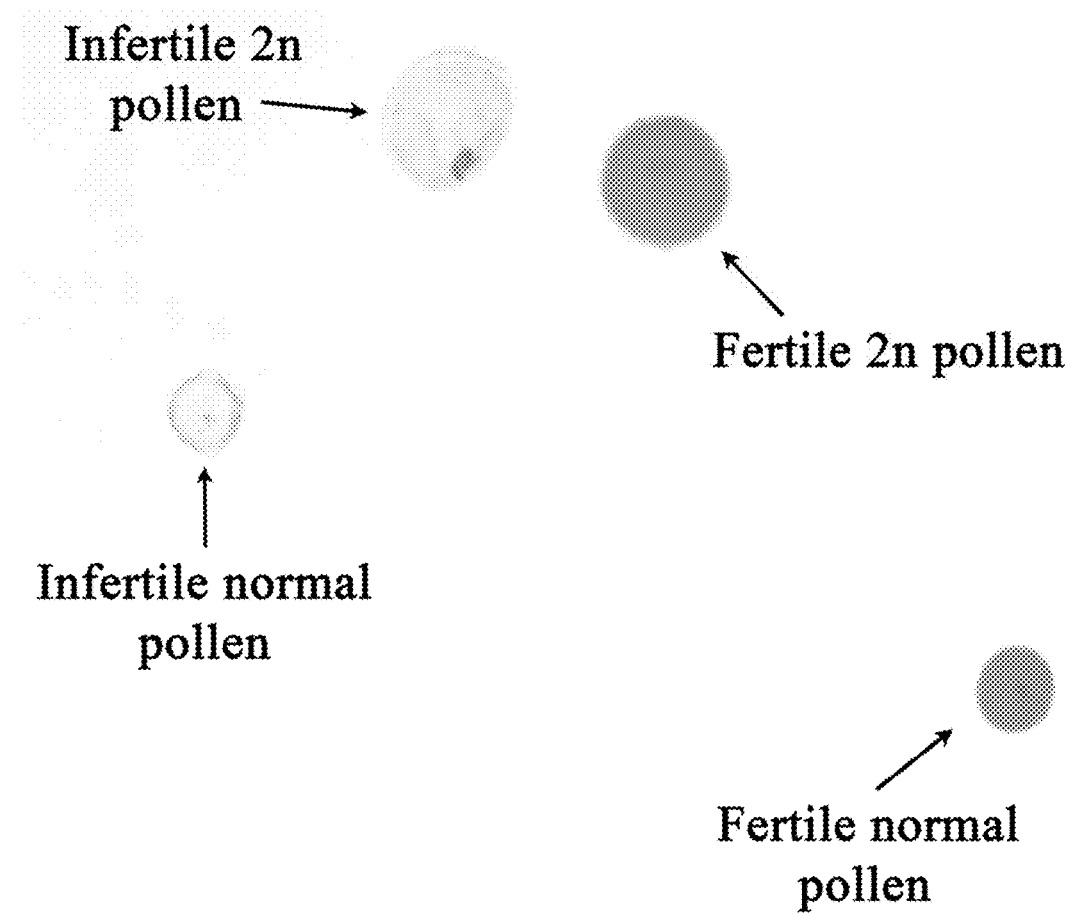
FIG. 3 shows detection results of fertility of pollen obtained after a high-temperature treatment, where pollen is fertile if stained red by aceto-carmine and pollen is infertile if not stained red by aceto-carmine.

Pollen with a diameter 1.5 times a diameter of normal pollen was counted as 2n pollen (as shown in FIG. 2). Pollen stained red by aceto-carmine was counted as fertile pollen, and pollen not stained red by aceto-carmine was counted as infertile pollen (as shown in FIG. 3).

An occurrence frequency of 2n pollen was a ratio of an amount of 2n pollen to a total amount of pollen observed, and a fertility rate of 2n pollen was a ratio of an amount of fertile 2n pollen to a total amount of 2n pollen observed. Statistical results are shown in Table 2. As can be seen from the statistical results in Table 2:

1. When no high-temperature treatment is applied, an occurrence frequency of 2n pollen is 0.9%, and a fertility rate is 100%.
2. When a high-temperature treatment is conducted with the non-ex vivo tree branch bud heating device (patent ZL200610113448.X) at a leptotene stage to a pachytene stage of pollen mother cells, 4 h of the high-temperature treatment at 45° C. and 5 h of the high-temperature treatment at 47° C. lead to excellent 2n pollen yields of 9.44% and 9.23%, respectively, indicating that the above treatment conditions allow the optimal induction effect for 2n pollen in *Camellia oleifera* (Table 2).
3. A fertility rate of 2n pollen in *Camellia oleifera* decreases with the increase of an treatment temperature, and especially when the treatment temperature is as high as 49° C., a fertility rate of pollen decreases significantly (Table 2).
4. Treatment conditions for 2n pollen in *Camellia oleifera* in the present disclosure: a leptotene stage to a pachytene stage of pollen mother cells, a style length: less than 2.57 mm, an induction temperature: 43° C. to 49° C., and an induction time: 3 h to 6 h.

Preferably, the style length is 1.97 mm<L≤2.17 mm, the induction temperature is 45° C. to 47° C., and the induction time is 4 h to 5 h.

Table 2 Statistical results of a 2n pollen yield and fertility rate under high-temperature treatment conditions

TABLE 2

Statistical results of a 2n pollen yield and fertility rate under high-temperature treatment conditions

| Meiosis stage | Temperature (° C.) | Time (h) | 2n pollen yield (%) | 2n pollen fertility rate (%) |
|---|---|---|---|---|
| Leptotene stage–pachytene stage | 43 | 3 | 2.59 | 85.17 |
| | 45 | 4 | 9.44 | 65.24 |
| | 47 | 5 | 9.23 | 43.13 |
| | 49 | 6 | 1.11 | 10.09 |
| Diplotene stage–diakinesis stage | 43 | 4 | 3.59 | 82.17 |
| | 45 | 3 | 2.67 | 68.52 |
| | 47 | 6 | 3.97 | 40.38 |
| | 49 | 5 | 1.83 | 16.95 |
| Metaphase I–anaphase I | 43 | 5 | 2.48 | 64.27 |
| | 45 | 6 | 4.38 | 49.12 |
| | 47 | 3 | 2.16 | 64.47 |
| | 49 | 4 | 2.15 | 29.63 |
| Prophase II–anaphase II | 43 | 6 | 1.99 | 53.16 |
| | 45 | 5 | 2.19 | 52.71 |
| | 47 | 4 | 2.27 | 48.19 |
| | 49 | 3 | 1.91 | 31.85 |
| CK | | | 0.90 | 100.00 |

Example 2A Screening of Concentrations of DMTU Solutions Applied 2.1 Application of DMTU Solutions Flower branches with a style length developing to 1.97 mm<L≤2.27 mm and pollen mother cells at a leptotene stage to a pachytene stage were selected as target flower branches, and DMTU solutions with different concentrations were applied to the target flower branches, respectively; and a flower branch not treated with a DMTU solution was adopted as a control.

The concentrations of the DMTU solutions were 1 mg/L, 5 mg/L, 10 mg/L, 15 mg/L, 20 mg/L, and 25 mg/L, respectively. Preparation method of a DMTU solution: DMTU was first dissolved with an appropriate amount of alcohol, and then water was added to a required concentration.

The above DMTU solutions with different concentrations each were sprayed on a flower branch, where a DMTU solution was evenly sprayed on a flower branch by a sprayer until there were condensed water droplets flowing down from leaves or flower buds; and each treatment was numbered and recorded (as shown in Table 3).

2.2 Doubling Treatment

After each DMTU solution was applied, in order to avoid rapid evaporation of a solution on a leaf surface due to a high-temperature treatment, the whole flower branch was wrapped with a plastic film, and then the non-ex vivo tree branch bud heating device in the authorized patent (patent ZL200610113448.X) was immediately used to apply a 45° C. high-temperature treatment to each target flower branch for 4 h, namely, a high-temperature doubling treatment. A doubling treatment method was the same as the doubling treatment method in step 1.2 of Example 1.

2.3 Statistical Analysis of 2n Pollen Fertility

After a high-temperature treatment was conducted for 4 h, a heating bag and a plastic film were removed to release the high-temperature treatment, and *Camellia oleifera* was allowed to grow naturally until anthers were pollinated. Pollen of each treatment was collected, and a temporary smear of the pollen was made by an aceto-carmine staining method and then photographed by an Olympus DP70 optical microscope; and a diameter of pollen was measured by Image J software, and an occurrence frequency and a fertility rate of 2n pollen were counted.

Statistical results are shown in Table 3, and it can be seen that 2n pollen yields and fertility rates when 5 mg/L, 10 mg/L, 15 mg/L, and 20 mg/L DMTU solutions are sprayed on flower branches are significantly improved compared with the control, where a 2n pollen yield and fertility rate when a 10 mg/L DMTU solution is applied are significantly higher than 2n pollen yields and fertility rates of other treatments (Table 3).

Table 3 Statistical results of 2n pollen yields and fertility rates under DMTU application

TABLE 3

Statistical results of 2n pollen yields and fertility rates under DMTU application

| Treatment | Concentration | 2n pollen yield (%) | 2n pollen fertility rate (%) |
|---|---|---|---|
| ck | / | 8.95 | 62.93 |
| 1 | 1 mg/L | 9.17 | 64.25 |
| 2 | 5 mg/L | 9.81 | 75.94 |
| 3 | 10 mg/L | 11.52 | 86.23 |
| 4 | 15 mg/L | 10.83 | 82.46 |
| 5 | 20 mg/L | 10.15 | 78.61 |
| 6 | 25 mg/L | 9.05 | 64.43 |

Example 2B Screening of High-Temperature Treatment Precursors for Induction of 2n Pollen in *Camellia oleifera*

2.1 Application of High-Temperature Treatment Precursors

The exogenous application of DMTU, mannitol, ascorbic acid, and brassinolide can improve the heat resistance and pollen fertility of a plant. When a style length developed to 1.97 mm<L≤2.27 mm and pollen mother cells grew to a leptotene stage to a pachytene stage, the above reagents were applied at different concentrations to target flower branches. The exogenous application of mannitol, ascorbic acid, and brassinolide was compared with the exogenous application of DMTU.

Concentrations of the DMTU, the mannitol, the ascorbic acid, and the brassinolide were 10 mg/L, 0.5 g/L, 1.5 mg/L, and 4.0 mg/L, respectively (as shown in Table 3).

The above reagents were applied through spraying on a flower branch and injection into a flower bud. The spraying on a flower branch was as follows: a precursor solution was evenly sprayed on the flower branch by a sprayer until there were condensed water droplets flowing down from leaves or flower buds. The injection into a flower bud was as follows: a precursor solution was injected into the flower bud by a 5 mL syringe (0.5×20 mm injection needle) through a scale gap at a top of the flower bud until there were water droplets overflowing a surface of the flower bud. Treatments were numbered 1 to 8 and recorded (as shown in Table 4).

2.2 Doubling Treatment

After a high-temperature treatment precursor was applied, in order to avoid rapid evaporation of a solution on a surface of or inside a leaf and a flower bud due to a high-temperature treatment after spraying on a flower branch or injection into a flower bud, the whole flower branch was wrapped with a plastic film, and then the non-ex vivo tree branch bud heating device in the authorized patent (patent ZL200610113448.X) was immediately used to apply a 45° C. high-temperature treatment to each target flower branch for 4 h, namely, a high-temperature doubling treatment. A doubling treatment method was the same as the doubling treatment method in step 1.2 of Example 1.

2.3 Statistical Analysis of 2n Pollen Fertility

After a high-temperature treatment was conducted for 4 h, a heating bag and a plastic film were removed to release the high-temperature treatment, and *Camellia oleifera* was allowed to grow naturally until anthers were pollinated. Pollen from each treatment was collected, and a temporary smear of the pollen was made by an aceto-carmine staining method and then photographed by an Olympus DP70 optical microscope, and a diameter of pollen was measured by Image J software, and an occurrence frequency and a fertility rate of 2n pollen were then counted. Statistical results are shown in Table 4.

A treatment effect of the exogenous application of DMTU is better than a treatment effect of exogenous application of mannitol, ascorbic acid, or brassinolide. A 2n pollen yield and fertility rate after a 10 mg/L DMTU solution is sprayed on a flower branch or injected into a flower bud is significantly higher than 2n pollen yields and fertility rates under other treatments, and especially the treatment with the 10 mg/L DMTU solution leads to a most significant improvement effect for 2n pollen fertility. The injection of the DMTU solution into a flower bud can lead to a 2n pollen yield and fertility rate of 12.17% and 90.14%, respectively, which is better than an effect of spraying on a flower branch (Table 4).

Table 4 Statistical results of 2n pollen yields and fertility rates under high-temperature treatment precursor application

TABLE 4

Statistical results of 2n pollen yields and fertility rates under high-temperature treatment precursor application

| Application mode | Treatment | High-temperature treatment precursor | Concentration | 2n pollen yield (%) | 2n pollen fertility rate (%) |
|---|---|---|---|---|---|
| Spraying on a flower branch | 1 | DMTU | 10 mg/L | 11.52 | 86.97 |
| | 2 | Mannitol | 0.5 g/L | 9.81 | 75.94 |
| | 3 | Ascorbic acid | 1.5 mg/L | 9.76 | 79.58 |
| | 4 | Brassinolide | 4.0 mg/L | 10.83 | 82.58 |
| Injection into a flower bud | 5 | DMTU | 10 mg/L | 12.17 | 90.14 |
| | 6 | Mannitol | 0.5 g/L | 9.68 | 77.89 |
| | 7 | Ascorbic acid | 1.5 mg/L | 10.05 | 81.26 |
| | 8 | Brassinolide | 4.0 mg/L | 11.03 | 84.13 |

Example 3 Screening of High-Temperature Treatment Precursor Compound Formulas

3.1 Application of High-Temperature Treatment Precursors

Flower branches with a style length developing to 1.97 mm<L≤2.27 mm and pollen mother cells developing to a leptotene stage to a pachytene stage were selected as target flower branches, and DMTU, mannitol, ascorbic acid, brassinolide, and sucrose-containing mixed solutions were applied at different concentrations to the target flower branches. 4 concentration levels were set for each reagent correspondingly (as shown in Table 5). An $L_{16}(4^5)$ orthogonal design method was used to prepare a total of 16 high-temperature treatment precursors. Each mixed solution was injected into a flower bud with a needle until water droplets overflowed a surface of the flower bud, where a manner for the injection was the same as the manner in the step "2.1 Application of high-temperature treatment precursors" of Example 2B. Each treatment combination was numbered and recorded.

of or inside a flower bud due to a high-temperature treatment after injection into the flower bud, the whole flower branch was wrapped with a plastic film, and then the non-ex vivo tree branch bud heating device in the authorized patent (patent ZL200610113448.X) was immediately used to apply a 45° C. high-temperature treatment to each target flower branch for 4 h, namely, a high-temperature doubling treatment. A doubling treatment method was the same as the doubling treatment method in step 1.2 of Example 1.

3.3 Statistical Analysis of 2n Pollen Fertility

After a high-temperature treatment was conducted for 4 h, a heating bag and a plastic film were removed to release the high-temperature treatment, and *Camellia oleifera* was allowed to grow naturally until anthers were pollinated. Pollen from each treatment was collected, and a temporary smear of the pollen was made by an aceto-carmine staining method and then photographed by an Olympus DP70 optical microscope; and a diameter of pollen was measured by Image J software, and a fertility rate of 2n pollen was counted. After treatments with the 16 high-temperature treatment precursors, a fertility rate of 2n pollen can be as high as 92.59% (Table 6).

TABLE 6

Statistical results of 2n pollen fertility rates under $L_{16}(4^5)$ orthogonal design test treatments

| Treatment | DMTU mg/L | Mannitol g/L | Ascorbic acid mg/L | Brassinolide mg/L | Sucrose g/L | 2n pollen fertility rate (%) |
|---|---|---|---|---|---|---|
| 1 | 5 | 0.1 | 0.5 | 2.0 | 5 | 75.91 |
| 2 | 5 | 0.5 | 1.5 | 8.0 | 10 | 78.37 |
| 3 | 5 | 1.0 | 2.0 | 4.0 | 15 | 80.17 |
| 4 | 5 | 2.0 | 1.0 | 6.0 | 30 | 78.45 |
| 5 | 10 | 0.5 | 1.0 | 4.0 | 5 | 92.59 |
| 6 | 10 | 0.1 | 2.0 | 6.0 | 10 | 87.15 |
| 7 | 10 | 2.0 | 1.5 | 2.0 | 15 | 85.78 |
| 8 | 10 | 1.0 | 0.5 | 8.0 | 30 | 84.62 |
| 9 | 15 | 1.0 | 1.5 | 6.0 | 5 | 80.79 |
| 10 | 15 | 2.0 | 0.5 | 4.0 | 10 | 79.94 |
| 11 | 15 | 0.1 | 1.0 | 8.0 | 15 | 84.29 |
| 12 | 15 | 0.5 | 2.0 | 2.0 | 30 | 79.46 |
| 13 | 20 | 2.0 | 2.0 | 8.0 | 5 | 74.17 |
| 14 | 20 | 1.0 | 1.0 | 2.0 | 10 | 78.35 |
| 15 | 20 | 0.5 | 0.5 | 6.0 | 15 | 81.39 |
| 16 | 20 | 0.1 | 1.5 | 4.0 | 30 | 79.22 |

TABLE 5

Factor levels of high-temperature treatment precursors

| Level | DMTU mg/L A | Mannitol g/L B | Ascorbic acid mg/L C | Brassinolide mg/L D | Sucrose g/L E |
|---|---|---|---|---|---|
| 1 | 5 | 0.1 | 0.5 | 2.0 | 5 |
| 2 | 10 | 0.5 | 1.0 | 4.0 | 10 |
| 3 | 15 | 1.0 | 1.5 | 6.0 | 15 |
| 4 | 20 | 2.0 | 2.0 | 8.0 | 30 |

3.2 Doubling Treatment

After a high-temperature treatment precursor was applied, in order to avoid rapid evaporation of a solution on a surface A range analysis method was used to calculate and analyze 2n pollen fertility rates, and main factors, an optimal level, and an optimal combination affecting an improvement effect of a high-temperature treatment precursor for a 2n pollen fertility rate were determined.

A K value is a sum of 2n pollen fertility rates corresponding to each level of each factor, and a k value is quarter of a corresponding K value. For example, k1=K1/4 (4 is a level number of the factor). A optimal level of a factor can be determined according to a k value, and the larger the k value, the better the level. An optimal combination can be composed of optimal levels of factors.

A range is used to reflect an impact degree of each factor on a 2n pollen fertility rate, and an effect order of each factor on improvement of a 2n pollen fertility rate can be determined according to a range.

It can be seen from the ranges (Table 7) that main effects of factors on a 2n pollen fertility rate are ranked as follows:

DMTU>mannitol>ascorbic acid>brassinolide>sucrose, where DMTU exhibits the greatest effect on the 2n pollen fertility rate. Further analysis results show that optimal levels of DMTU, mannitol, ascorbic acid, brassinolide, and sucrose are 10 mg/L, 0.5 g/L, 1.0 mg/L, 4.0 mg/L, and 15 g/L, respectively, and thus an optimal combination of different levels of the factors is A2B2C2D2E3 (Table 7).

Table 7 $L_{16}(4^5)$ orthogonal design analysis

TABLE 7

$L_{16}(4^5)$ orthogonal design analysis

| Treatment | Experimental factor | | | | |
|---|---|---|---|---|---|
| | DMTU A | Mannitol B | Ascorbic acid C | Brassinolide D | Sucrose E |
| K1 | 312.90 | 326.57 | 321.86 | 319.50 | 323.46 |
| K2 | 350.14 | 331.81 | 333.68 | 331.92 | 323.81 |
| K3 | 324.48 | 323.93 | 324.16 | 327.78 | 331.63 |
| K4 | 313.13 | 318.34 | 320.95 | 321.45 | 321.75 |
| k1 | 78.23 | 81.64 | 80.47 | 79.88 | 80.87 |
| k2 | 87.54 | 82.95 | 83.42 | 82.98 | 80.95 |
| k3 | 81.12 | 80.98 | 81.04 | 81.95 | 82.91 |
| k4 | 78.28 | 79.59 | 80.24 | 80.36 | 80.44 |
| Range | 9.31 | 3.37 | 3.18 | 3.11 | 2.47 |
| Effect order | | | A > B > C > D > E | | |
| Optimal level | A2 | B2 | C2 | D2 | E3 |
| Optimal | | | A2B2C2D2E3 | | |

Example 4 Use of an Optimal Composition of a High-Temperature Treatment Precursor 4.1 Application of High-Temperature Treatment Precursors Flower branches with a style length developing to 1.97 mm<L≤2.27 mm and pollen mother cells developing to a leptotene stage to a pachytene stage were selected as target flower branches (100 branches) to be treated, and the high-temperature treatment precursor mixed solution (the optimal combination) screened in Example 3 was applied to the target flower branches. Concentrations of DMTU, mannitol, ascorbic acid, brassinolide, and sucrose in the mixed solution were 10 mg/L, 0.5 g/L, 1.0 mg/L, 4.0 mg/L, and 15 g/L, respectively.

Before a high-temperature treatment, flower buds of the target flower branches were injected with the high-temperature treatment precursor mixed solution by a needle until water droplets overflowed surfaces of the flower buds, where a manner for the injection was the same as the manner in the step "2.1 Application of high-temperature treatment precursors" of Example 2B. The treatment was numbered and recorded.

Flower buds of control flower branches (50 branches) were injected with water by a needle until water droplets overflowed from the surfaces of the flower buds, and the treatment was numbered and recorded.

4.2 Doubling Treatment

After a high-temperature treatment precursor was applied, in order to avoid rapid evaporation of a solution on a surface of or inside a flower bud due to a high-temperature treatment after injection into the flower bud, a treated flower branch was wrapped with a plastic film, and then the non-ex vivo tree branch bud heating device in the authorized patent (patent ZL200610113448.X) was immediately used to apply a 45° C. high-temperature treatment to each treated flower branch for 4 h.

After a flower bud of a control flower branch was injected with water, the control flower branch was wrapped with a plastic film, and then the non-ex vivo tree branch bud heating device in the authorized patent (patent ZL200610113448.X) was immediately used to apply a 45° C. high-temperature treatment to each control flower branch for 4 h.

4.3 Statistical Analysis of 2n Pollen Fertility

After a high-temperature doubling treatment was conducted for 4 h, a heating bag and a plastic film were removed to release the high-temperature treatment, and *Camellia oleifera* was allowed to grow naturally until anthers were pollinated. Pollen from each treatment was collected, and a temporary smear of the pollen was made by an aceto-carmine staining method and then photographed by an Olympus DP70 optical microscope; and a diameter of pollen was measured by Image J software, and a yield and a fertility rate of 2n pollen were counted. An average yield and fertility rate of 2n pollen under application of the high-temperature treatment precursor with the optimal composition are 12.59% and 96.82%, respectively (Table 8), and this fertility rate is significantly higher than the optimal fertility rate of 92.59% for 2n pollen under the treatment of the high-temperature treatment precursor mixed solution in Example 3. In addition, compared with the injection of a flower bud with water in the control group, the high-temperature treatment precursor with the optimal composition exhibits a very significant effect for improving a 2n pollen yield and fertility rate (Table 8).

Table 8 A 2n pollen yield and fertility rate under application of the high-temperature treatment precursor with the optimal composition

TABLE 8

A 2n pollen yield and fertility rate under application of the high-temperature treatment precursor with the optimal composition

| Treatment | 2n pollen yield | 2n pollen fertility rate (%) |
|---|---|---|
| High-temperature treatment | 12.59% a | 96.82% a |
| Control: Injection of a flower | 9.87% b | 66.85% b |

Different lowercase letters represent significant differences at a P=0.05 level.

In the present disclosure, the production of 2n pollen in *Camellia oleifera* is induced by a high-temperature treatment, and the high-temperature treatment precursor is applied to significantly improve the fertility of 2n pollen, which helps to improve an efficiency of 2n pollen hybridization to obtain a *Camellia oleifera* polyploid.

What is claimed is:

1. A method for improving yield and fertility of 2n pollen in *Camellia oleifera*, said method comprising:
   1) treating flower buds of a *Camellia oleifera* plant with a 5 mg/L to 20 mg/L N,N'-dimethylthiourea (DMTU)-containing solution by the following process:
      when flower buds of a *Camellia oleifera* plant comprise styles 1.97 mm to 2.17 mm in length:
      (a) spraying a flower branch of the *Camellia oleifera* plant with the DMTU-containing solution; or
      (b) injecting the DMTU-containing solution into flower buds on a flower branch of the *Camellia oleifera* plant; and
   2) heat treating the flower branch at 45° C. to 47° C. for 4 hours to 5 hours; wherein the DMTU-containing solution further comprises: 0.1 g/L to 2.0 g/L mannitol, 0.5 mg/L to 2.0 mg/L ascorbic acid, 2.0 mg/L to 8.0 mg/L brassinolide, and 5.0 g/L to 30.0 g/L sucrose.

2. The method of claim 1, wherein the heat treatment is at 45° C. for 4 hours.

3. The method of claim 1, wherein the DMTU-containing solution comprises DMTU at 10 mg/L.

4. The method of claim 1, wherein the DMTU-containing solution comprises 10 mg/L DMTU, 0.5 g/L mannitol, 1.0 mg/L ascorbic acid, 4.0 mg/L brassinolide, and 15.0 g/L sucrose.

5. The method of claim 1, further comprising wrapping the flower branch of the *Camellia oleifera* plant after treating the flower buds with the DMTU-containing solution and prior to the heat treatment.

* * * * *